United States Patent [19]

Kajihara et al.

[11] Patent Number: 5,124,077
[45] Date of Patent: Jun. 23, 1992

[54] SKIN DETERGENT COMPOSITION CONTAINING A PHOSPHATE ESTER SURFACTANT AND A WATER SOLUBLE CHITIN DERIVATIVE

[75] Inventors: Yasushi Kajihara, Saitama; Kenji Kaneda, Chiba; Hajime Hirota, Tokyo, all of Japan

[73] Assignee: Kao Corporation, Tokyo, Japan

[21] Appl. No.: 488,093

[22] Filed: Mar. 5, 1990

[30] Foreign Application Priority Data

Apr. 14, 1989 [JP] Japan ................. 1-94740

[51] Int. Cl.$^5$ .................. C11D 1/34; C11D 3/30; C11D 3/384; A61K 7/50
[52] U.S. Cl. .................. 252/545; 252/546; 252/548; 252/153; 252/174.16; 252/DIG. 5; 252/DIG. 17; 424/70
[58] Field of Search ............ 424/70; 252/174.16, 252/545, 546, 547, 548, DIG. 5, DIG. 13, DIG. 17, 153

[56] References Cited

U.S. PATENT DOCUMENTS

| | | | |
|---|---|---|---|
| 3,879,376 | 4/1975 | Vanlerberge | 424/47 |
| 4,132,679 | 1/1979 | Tsutsumi | 252/545 |
| 4,139,485 | 2/1979 | Imokawa | 252/135 |
| 4,259,204 | 3/1981 | Homma | 252/174.16 |
| 4,298,494 | 11/1981 | Parslow | 252/174.16 |
| 4,321,256 | 3/1982 | Hasegawa | 424/70 |
| 4,369,134 | 1/1983 | Deguchi | 252/526 |
| 4,381,259 | 4/1983 | Homma | 252/542 |
| 4,707,292 | 11/1987 | Sano | 252/174.16 |
| 4,758,376 | 7/1988 | Hirota | 252/545 |
| 4,822,598 | 4/1989 | Lang | 424/47 |
| 4,931,271 | 6/1990 | Lang | 424/47 |

FOREIGN PATENT DOCUMENTS

| | | | |
|---|---|---|---|
| 54-134712 | 10/1979 | Japan | 252/174.16 |
| 62-138418 | 6/1987 | Japan | 252/545 |
| 7049245 | 10/1987 | Japan | . |

Primary Examiner—A. Lionel Clingman
Assistant Examiner—Erin Higgins
Attorney, Agent, or Firm—Birch, Stewart Kolasch & Birch

[57] ABSTRACT

A skin detergent composition comprises (a) 5 to 95 percent by weight of a phosphoric acid ester having the formula (I) or (II) and (b) 0.0005 to 0.1 percent by weight of a water-soluble chitin compound.

6 Claims, No Drawings

SKIN DETERGENT COMPOSITION CONTAINING A PHOSPHATE ESTER SURFACTANT AND A WATER SOLUBLE CHITIN DERIVATIVE

The present invention concerns a skin detergent composition. More in particular, it relates to a skin detergent composition excellent in feeling of use and mild to skins.

PRIOR ART

Heretofore, it has been recognized that phosphoric acid ester type surface active agents are less stimulative and extremely mild to the skin, and they have been utilized as one of the ingredients for skin detergents. However, in the case of using the phosphoric acid ester type surface active agent for a skin detergent, since water insoluble calcium salts are deposited upon rinsing, the problem of rinsing becomes difficult and the feeling of use is not favorable.

On the other hand, water soluble chitin derivatives have been developed in recent years as a moisture retaining agent in cosmetics and, as shown in Japanese Patent Publication Sho 62-49245 and Japanese Patent Laid-Open Sho 62-138418, since they show a moisture retaining effect and are excellent in absorbability to surface tissues of the skin or hair and have a softening effect (conditioning effect) to the skin or hair, they have been utilized as one of the ingredients for shampoo compositions. However, in the case of using the water soluble chitin derivative as the ingredient for the skin detergent, since rinsing of the detergent is difficult by their excellent absorbability or absorption, the feeling of use is not favorable and, accordingly, application as a skin detergent is difficult at present time.

SUMMARY OF THE INVENTION

The present inventors have made an earnest study for overcoming the foregoing drawbacks in skin detergent compositions using a phosphoric acid ester type surface active agent and, as a result, have surprisingly, found that a skin detergent in which the feeling of use, a problem with phosphoric acid ester type surface active agents, is remarkably improved, and having excellent rinsing properties can be obtained by blending a chitin derivative, although showing remarkable skin adsorption, at such a low concentration range not usually employed and have accomplished the present invention.

That is, the present invention provides for a skin detergent composition comprising 5–95% by weight of (a) a phosphoric acid ester type surface active agent represented by the following general formula (I) or (II):

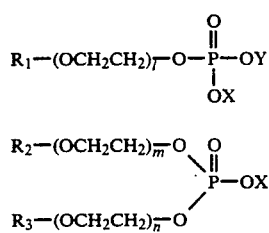

where each of $R_1$, $R_2$ and $R_3$ represents a saturated or unsaturated hydrocarbon group with 8 to 18 carbon atoms, each of X and Y represents a hydrogen, alkali metal, ammonium or an alkanol amine having a hydroxy alkyl group with 2 or 3 carbon atoms and each of l, m and n represents a number of 0 to 10, and (b) 0.0005 to 0.1% by weight of water soluble chitin derivative.

The invention provides a skin detergent composition comprising (a) 5 to 95 percent by weight of a phosphoric acid ester having the formula (I) or (II) and (b) 0.0005 to 0.1 percent by weight of a water-soluble chitin compound. It further comprises as the balance, a carrier. It is preferable that the component (a) comprises one having the formula (I) and the other having the formula (II) at a weight ratio of 10:0 to 5:5.

As the phosphoric acid ester type surface active agent utilized as ingredient (a), those with 0 to 3 of addition mol number of ethylene oxide are preferred. In particular, those with no addition of ethylene oxide and having an alkyl group of 12 to 14 carbon atoms are particularly preferred. Specifically, there can be mentioned, for example, sodium mono- or di-lauryl phosphate, potassium mono- or di-lauryl phosphate, diethanolamine mono- or di-lauryl phosphate, triethanolamine mono- or di-lauryl phosphate, sodium mono- or di-myristyl phosphate, potassium mono- or di-myristyl phosphate, triethanolamine mono- or di-myristyl phosphate, etc. The ingredient (a) is preferably used while mixing the compounds represented by the general formulae (I) and (II) described above within a range from 10:0 to 5:5, particularly, from 10:0 to 7:3 by weight ratio.

The water soluble chitin derivative of the ingredient (b) is derived from chitin material present in shells of crustacea such as crabs or shrimps, outer skeletons of insects, or cell walls of fungus or algae as a starting material. As the typical example, there can be mentioned chitosan which is a deacetylation product of chitin.

As a specific method of obtaining chitosan, there can be mentioned, for example; a method of treating shells of crabs or shrimps with a diluted hydrochloric acid to apply a calcium carbonate-removing treatment and then treating the same with an aqueous diluted solution of sodium hydroxide to remove protein, washing the thus obtained crude chitin with water, applying purification if necessary, deacelylating by adding an aqueous concentrated solution of sodium hydroxide, water washing the thus obtained crude chitosan and applying purification if necessary, thereby obtaining chitosan.

Although chitin itself is generally water insoluble, chitin treated by a certain method is water soluble. That is, a partially deacetylated water soluble chitin with a deacetylation degree of 40–60% as disclosed in Japanese Patent Laid-Open No. Sho 53-47479 can be mentioned as an example. The water soluble deacetylated chitin can also be used in the present invention. Further, those rendered water soluble by the introduction of substituents to chitin for example, carboxymethyl chitin introduced with a carboxymethyl group, glycolated chitin, chitin sulfate, etc. may also be used in the present invention.

Although chitin is usually a high molecular weight material having a molecular weight of greater than 1,000,000, the molecular weight is reduced in the derivative thereof in the course of the treatment and those having molecular weight of about several hundreds of thousand are often present. The water soluble chitin derivatives usable in the present invention have a molecular weight of greater than 1,000,000 nearly to those of natural chitin and those of a reduced molecular weight such as of several tens of thousand.

For the skin detergent composition according to the present invention, there is no particular restriction for the formulation but it may be formulated in any known forms as required, for example, as a solid detergent, powdery detergent, granular detergent, paste detergent and liquid detergent.

The content of ingredient (a) in the skin detergent composition according to the present invention ranges from 5 to 95% by weight. Preferably, the content of the ingredient (a) is from 5 to 50% by weight, particularly, from 10 to 40% by weight in the case of the liquid detergent, from 30 to 80% by weight, in particular, from 40 to 70% by weight in the case of the paste detergent and from 60 to 95% by weight, particularly, from 70 to 90% by weight in the case of the solid and powdery detergent. Further, the content of ingredient (b) ranges from 0.0005 to 0.1% by weight. If the content of the ingredient (b) is less than 0.0005% by weight, the effect is insufficient. On the other hand, if it exceeds 0.1% by weight, rinsing is difficult and the feeling of use is worsened and both cases are not preferred. Particularly preferred content of the ingredient (b) is within a range from 0.001 to 0.03% by weight.

In the skin detergent composition according to the present invention, various optional ingredients can be blended as required. As the optional ingredients, there can be mentioned, in addition to water, for example, a foaming agent such as a higher fatty acid salt, alkylamine oxide, fatty acid alkanolamide, imidazoline type amphoteric surface active agent, etc.; a feeling improver such as squalene and lanoline; inorganic and organic salts, diluent, perfume, pigment, sterilizer, anti-inflammatory agent, moisture preserver, viscosity controller, solubilizing agent, presevatives, water soluble polymeric compound, etc.

EXAMPLES

The present invention will be described more in details referring to examples but the invention is not restricted only to these examples.

EXAMPLE 1

A liquid detergent composition was prepared by the following composition, and the feeling of use and skin chapping were estimated respectively while varying the kind and the blending amount of the water soluble chitin derivative.

Detergent Composition

Phosphoric acid ester type surface active agent: 30 parts by weight
Water soluble chitin derivative: 0.001–0.1 parts by weight
Ethanol: 5 parts by weight
Water: balance

Method of Evaluating the Feeling of Use

After foaming the test specimens of the detergent manually by 20 panellers, they were rinsed with tap water and the feeling of use was evaluated by the panellers to obtain average values.

Score Used
2: easy to rinse
1: somewhat easy to rinse
0: neutral
−1: somewhat difficult to rinse
−2: difficult to rinse

Method of Evaluating Skin Chapping

An aqueous 15% solution of the test specimen for the detergent was prepared and the forearms of ten monitors were repeatedly applied with a treatment of the aqueous solution for three times per one day each time for 10 min, each at an interval of three hours. The treatment was applied continuously for five days and the treated portions were judged with naked eyes to define the average value as an index of skin chapping.

Score for Skin Chapping
0: with no skin chapping
1: with slight skin chapping
2: with medium skin chapping
3: with heavy skin chapping Results of the evaluation are shown in Table 1.

TABLE 1

| | | Phosphoric acid ester type surface active agent | Addition amount of water soluble chitin derivative (parts by weight) | Score used | Skin chapping index |
|---|---|---|---|---|---|
| Comparative product | 1 | Triethanolamine monolauryl phosphate | — | −1.1 | 0.5 |
| | 2 | Triethanolamine monolauryl phosphate | Carboxymethyl chitin (0.500) | −1.3 | 0.2 |
| | 3 | Triethanolamine laurate | Carboxymethyl chitin (0.010) | 0.4 | 1.8 |
| Invented Product | 1 | Triethanolamine monolauryl phosphate | Carboxymethyl chitin (0.001) | 1.1 | 0.3 |
| | 2 | Triethanolamine monolauryl phosphate | Carboxymethyl chitin (0.010) | 1.6 | 0.2 |
| | 3 | Triethanolamine monolauryl phosphate | Carboxymethyl chitin (0.100) | 1.3 | 0.2 |
| | 4 | Triethanolamine monolauryl phosphate | Chitin Sulfate (0.010) | 1.0 | 0.2 |
| | 5 | Sodium monolauryl phosphate | Carboxymethyl chitin (0.010) | 1.3 | 0.2 |

RESULT

As has been described above, since the skin detergent according to the present invention shows excellent performance by providing a refreshed feeling, satisfactory feeling of use and extremely less skin stimulation.

On the other hand, if the blending amount of the chitin derivative is greater as in Comparative Product 1, no satisfactory feeling of use was obtained since rinsing was difficult and it provided a slimy feeling and a feeling of remaining.

EXAMPLE 2

Solid Detergent

| | Parts by weight |
|---|---|
| Sodium monolauryl phosphate | 60 |
| Sodium dilauryl phosphate | 20 |
| Sodium lauryl phosphate | 10 |
| Carboxymethyl chitin | 0.006 |
| Perfume | 0.3 |
| Pigment | slight amount |
| | 0.3 |

-continued

|  | Parts by weight |
| --- | --- |
| Water | balance |

With the above composition, a solid detergent mild to the skin and excellent in feeling of use could be obtained.

EXAMPLE 3

Creamy Detergent

|  | Parts by weight |
| --- | --- |
| Sodium monolauryl phosphate | 35 |
| Sodium monocetyl phosphate | 10 |
| Carboxymethyl chitin | 0.05 |
| Sodium chloride | 7 |
| Polyethylene glycol (molecular weight: 8000) | 5 |
| Sorbitol | 5 |
| Perfume | 0.7 |
| Water | balance |

With the above composition, a solid detergent mild to the skin and excellent in feeling of use could be obtained.

We claim:

1. A skin detergent composition consisting essentially of (a) 5 to 95 percent by weight of a phosphoric acid ester having the formula (I) or (II) or mixtures thereof

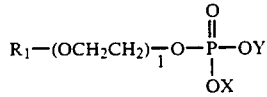

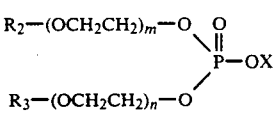

wherein each of $R_1$, $R_2$ and $R_3$ represents a saturated or unsaturated hydrocarbon group having 8 to 18 carbon atoms, each of X and Y represents a hydrogen, an alkali metal, ammonium or an alkanol amine having a hydroxy alkyl group having 2 or 3 carbon atoms, and each of $l$, $m$ and $n$ represents a number of 0 to 10; and (b) 0.0005 to 0.1% by weight of a water soluble chitin derivative; and an acceptable carrier.

2. The composition as claimed in claim 1, which further comprises the balance of a carrier.

3. The composition as claimed in claim 1, in which the component (a) comprises one having the formula (I) and the other having the formula (II) at a weight ratio of 10:0 to 5:5.

4. The composition according to claim 1, wherein said phosphoric acid ester I or II, or mixtures thereof, is present in an amount of from 5 to 50% by weight of the composition.

5. The composition according to claim 1, wherein said phosphoric acid ester I or II, or mixtures thereof, is present in an amount of from 10 to 40% by weight of the composition.

6. The composition according to claim 1, wherein said chitin derivative is present in an amount of from 0.001 to 0.03% by weight of the composition.

* * * * *